United States Patent [19]

Künzel et al.

[11] 4,163,088

[45] Jul. 31, 1979

[54] ANTISTATIC POLYAMIDE COMPOSITIONS WITH POLYALKYLENEGLYCOL ETHER HAVING SECONDARY TERMINAL URETHANE GROUPS

[75] Inventors: Hans E. Künzel, Dormagen; Claus-Rüdiger Bernert, Bomlitz; Günter Arend, Dormagen; Francis Bentz, Cologne; Helmut Sinner; Dieter Brokmeier, both of Dormagen, all of Fed. Rep. of Germany

[73] Assignee: Bayer Aktiengesellschaft, Leverkusen, Fed. Rep. of Germany

[21] Appl. No.: 808,051

[22] Filed: Jun. 20, 1977

Related U.S. Application Data

[63] Continuation of Ser. No. 554,516, Mar. 3, 1975, abandoned.

[30] Foreign Application Priority Data

Mar. 1, 1974 [DE]   Fed. Rep. of Germany ....... 2409715

[51] Int. Cl.² ...................... C08L 77/02; C08G 69/46

[52] U.S. Cl. .................................. 525/433; 560/115; 560/33; 560/27; 560/32; 560/166; 560/164; 560/158; 528/314; 528/315; 528/325; 528/336; 544/172; 544/388; 260/239 BF

[58] Field of Search .................. 260/78 S, 78 R, 78 A, 260/78 L; 526/6

[56] References Cited

U.S. PATENT DOCUMENTS

| | | | |
|---|---|---|---|
| 3,810,956 | 5/1974 | Kimura et al. | 260/78 S |
| 3,928,298 | 12/1975 | Wolf et al. | 260/78 S |

*Primary Examiner*—Harold D. Anderson
*Attorney, Agent, or Firm*—Plumley & Tyner

[57] ABSTRACT

The invention relates to antistatic polyamide compositions comprising a polyamide and as an antistatic agent from 0.1 to 20%, preferably from 1.5 to 15%, by weight based on the total weight of the composition of urethanes with ether groups. The urethanes with ether groups are stable in melts of aliphatic polyamides for prolonged periods at temperatures of up to about 300° C. and filaments and fibers of such polyamides or woven fabrics, knitted fabrics, non-woven or pile fabrics produced from these filaments or fibers show outstanding antistatic properties.

8 Claims, No Drawings

ANTISTATIC POLYAMIDE COMPOSITIONS WITH POLYALKYLENEGLYCOL ETHER HAVING SECONDARY TERMINAL URETHANE GROUPS

This is a continuation of application Ser. No. 544,516, filed Mar. 3, 1975, now abandoned.

This invention relates to permanently antistatic polyamide compositions which may be processed into permanently antistatic filaments, fibres, films, and other shaped articles, and to processes for producing polyamide compositions of this kind.

It is known that fibres, woven fabrics, knitted fabrics and films of polyamides can be antistatically finished by treating their surfaces with polyethers containing urethane groups corresponding to formula (I) or (II) below (cf. DT-OS No. 1,768,058 and U.S. Pat. No. 3,658,882).

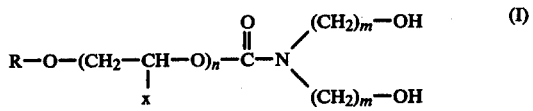

wherein
R=an alkyl or alkaryl radical, x=H, $CH_3$ or $C_2H_5$, n=1-10, m=1-6; and

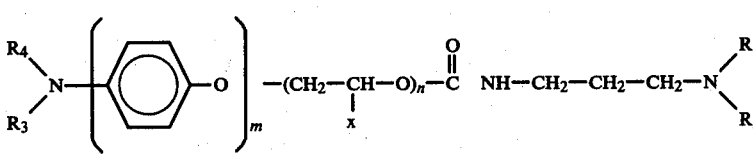

wherein
$R_4$, $R_5$=alkyl radicals,
$R_1$, $R_2$=alkyl or hydroxy alkyl radicals,
x=H, $CH_3$ or $C_2H_5$,
n=1-10,
m=0-1.

One disadvantage of this process, however, is that the antistatic finish is not washproof. Tests have shown that a single wash is sufficient to eliminate the antistatic effect almost completely.

It is also known from DT-AS 1,273,124 that polyalkylene glycol ethers with a molecular weight of at least 600, containing at least one alkyl, aryl or aralkyl ether group at their ends, give polyamides favourable antistatic properties when they are uniformly incorporated into the polyamide as a separate phase.

One disadvantage of products of this kind is that the polyalkylene glycol ethers with only partly etherified terminal hydroxyl groups can be partly incorporated into the polymer by reaction with the polyamides, for example with free terminal carboxyl groups, and are then redundant so far as producing an antistatic effect is concerned, because it has been shown that it is only additives of the type which are not incorporated into the polymer that are antistatically active. On the other hand, polyalkylene glycol ethers with only partly etherified terminal hydroxyl groups can be removed relatively easily from the polymers during washing, with the result that the antistatic activity is gradually lost. It should be possible to eliminate these by using polyalkylene glycol ethers with very few, if any, free terminal hydroxyl groups. However, polyalkylene glycol ethers in which all the terminal hydroxyl groups are etherified can only be obtained relatively complicated processes.

It is also known that polyethers containing urethane groups and corresponding to the formula (III):

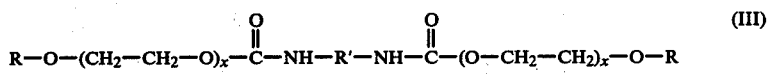

wherein
R=an alkyl, aryl, aralkyl or alkaryl radical
R'=an alkylene, arylene, aralkylene, alkarylene or cycloalkylene radical, and
x=5-50 give polymers excellent antistatic properties when incorporated in them in quantities of from 0.5 to 15% by weight (cf. German Patent Application No. P 23 06 920). One disadvantage of these compounds, however, is that they can only be incorporated into polymers of the kind which are processed from solutions, because when the products are incorporated into a polymer melt, for example of a polyamide polyester, at the high melting temperatures necessary the urethane group with a free hydrogen atom on the nitrogen atom is not stable and the compounds of formula (III) are destroyed through the reformation of isocyanates and hydroxyl compounds. The same applies to the compounds of formula (II).

Although, in compounds of formula (I), the urethane group should be more stable at the melting temperature of the aliphatic polyamides, because there is no longer a free hydrogen atom present on the nitrogen atom, the terminal hydroxyl groups of the compounds can in this case, too, enter into secondary reactions with the polymer, as a result of which the compound is used up and the antistatic effect is weakened accordingly.

However, it should be possible to avoid these disadvantages by using polyether urethanes which do not contain any free hydroxyl groups and which do not have any hydrogen atoms on the nitrogen atom. At all events urethanes could be expected to undergo transesterification or aminolysis reactions on the

-bond in polymer melts, resulting in chain termination and, hence, in reduced molecular weights.

It has now surprisingly been found that polyalkylene ethers with secondary urethane groups corresponding to the general formula:

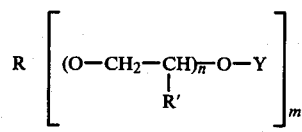

wherein
  m is a number from 1 to 6;
  n is a number of at least 3, preferably a number from 7 to 60;
  R represents an m-functional, straight-chain, cyclic or branched, saturated or unsaturated alkyl radical optionally containing hetero atoms, for example oxygen or nitrogen atoms, in which case hetero atoms with more than two bonds may also be the starting points for branches, an aralkyl radical, an optionally alkyl-substituted m-functional aromatic radical or, where m=1, even the radical Y;
  R' represents a hydrogen atom, an alkyl group with 1 to 5 carbon atoms, a cycloalkyl, aryl, alkaryl or aralkyl group; and
  Y represents the group:

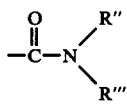

or a hydrogen atom, at least 70% and preferably more than 90% by weight of the radicals Y having to represent the group:

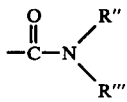

wherein
  R" and R'", independently of one another, may represent alkyl groups with 1 to 30 carbon atoms, cycloalkyl aryl, aralkyl or alkaryl groups or, together with the nitrogen atom, form a heterocyclic ring, in which case further hetero atoms, such as oxygen or nitrogen, may be introduced both into the alkyl group R" or R'" and into the heterocycle formed from R", R'" and the N-atom, of which hetero atoms the nitrogen atoms may in turn be part of a secondary terminal urethane group of a polyalkylene ether,
are stable in melts of aliphatic polyamides for prolonged periods at temperatures of up to about 300° C., and that polyamides containing urethanes of this kind, more especially filaments and fibres of such polyamides or woven fabrics, knitted fabrics, nonwovens or pile fabrics produced from these filaments or fibres, show outstanding antistatic properties and that polycondensation or polymerisation is not adversely affected by the addition of the above urethanes.

The particular advantage of the new antistatic polyamide compositions over conventional antistatic polyamide compositions containing products without these terminal urethane groups, is that for about the same or slightly improved initial antistatic values the antistatic properties are much more resistant to washing following an aftertreatment, more especially after fixing in hot air or saturated steam at temperatures of around or above 100° C.

Accordingly, the invention relates to antistatic polyamide compositions comprising a polyamide and, as an antistatic agent, from 0.5 to 20%, preferably from 1.5 to 15%, by weight based on the total weight of composition, of urethane with ether groups corresponding to the general formula:

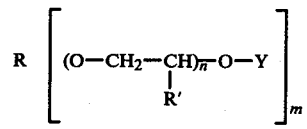

in which R, R', Y, m and n are as defined above.

Preferred antistatic agents are polyalkylene glycol ethers with terminal urethane groups corresponding to the general formulae:

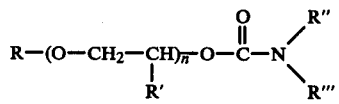

in which
  n is a number of at least 3, preferably a number of from 7 to 45;
  R represents a monofunctional straight-chain or branched, saturated or unsaturated alkyl radical with from 1 to 30 carbon atoms or an optionally alkyl-substituted aryl radical;
  R' represents a hydrogen atom or an alkyl radical with from 1 to 5 carbon atoms; and
  R" and R'", independently of one another, represent an alkyl radical with from 1 to 20 carbon atoms, or R", R'" and the nitrogen atom together form a heterocycle which may contain further hetero atoms such as oxygen or nitrogen;

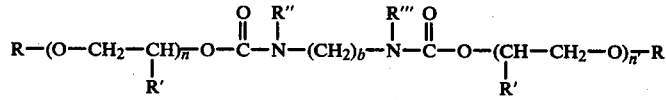

in which
  n and n' represent a number of at least 3, preferably a number of from 7 to 45;
  b is a number of from 2 to 10;
  R represents a monofunctional, straight-chain or branched, saturated or unsaturated alkyl radical with from 1 to 30 carbon atoms or an optionally alkyl-substituted aryl radical;
  R' represents a hydrogen atom or an alkyl radical with from 1 to 5 carbon atoms; and
  R" and R'", indepentently of one another represent an alkyl radical with from 1 to 20 carbon atoms, and
  R" and R" together may also form an alkylene bridge;

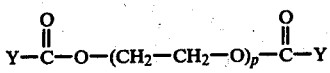

in which
p is a number of at least 8, preferably a number of from 12 to 50; and
Y represents the group:

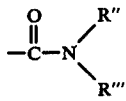

or represents a hydrogen atom, at least 70% and preferably at least 90% of the radicals Y representing the group:

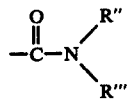

and
R" and R''', independently of one another, may be alkyl groups with from 1 to 30 carbon atoms, cycloalkyl, aryl, aralkyl or alkaryl groups or, together with the nitrogen atom, may form a heterocycle;

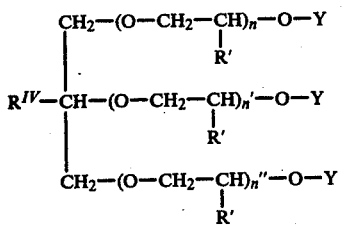

in which
n, n' and n", independently of one another, can be numbers of from 3 to 50 and, together, should total at least 10;
R' represents a hydrogen atom or an alkyl group with from 1 to 5 carbon atoms;
$R^{IV}$ represents a hydrogen atom, an alkyl group with from 1 to 18 carbon atoms or an aryl group; and
Y represents the group:

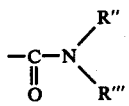

or represents a hydrogen atom, at least 70% and preferably at least 90% of the radicals Y representing the group:

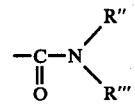

and R" and R''', independently of one another, may be alkyl groups with from 1 to 30 carbon atoms, cycloalkyl, aryl aralkyl or alkaryl groups or, together with the nitrogen atom, form a heterocycle;

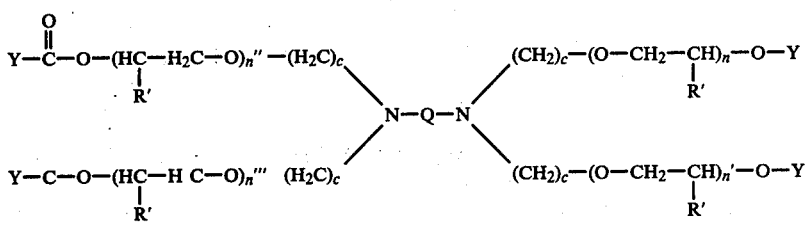

in which c is a number of from 2 to 6; n, n', n" and n''', independently of one another, may be numbers from 3 to 50 and, together, should total at least 15;
R' represents a hydrogen atom or an alkyl group with from 1 to 5 carbon atoms; Q represents an alkylene group with from 2 to 10 carbon atoms, whose C-chain may even be interrupted by hetero atoms, or an arylene group; and
Y represents the group:

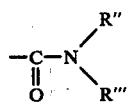

or a hydrogen atom, at least 70% and preferably at least 90% of the radicals Y representing the group:

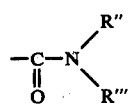

and R" and R''', independently of one another, may be alkyl groups with from 1 to 30 carbon atoms, cycloalkyl, aryl, aralkyl or alkaryl groups, or together with the nitrogen atom form a heterocycle.

The invention also relates to shaped articles produced from antistatic polyamide compositions of the above type, more especially antistatic fibres, filaments and films, and also to woven fabrics, knitted fabrics, nonwovens, pile fabrics or similar sheet-form materials produced from these antistatic fibres or filaments.

The urethanes with ether groups used in accordance with the invention are introduced into and intensively mixed with the polyamide melt before the polyamides are spun or extruded, the urethanes are applied to solid, granulated polyamide which is then melted, intensively mixed and spun or extruded; or in which the urethanes with ether groups used in accordance with the invention are introduced into the polymerisation or polycondensation mixtures before or after production of the polyamides, after which the antistatic polyamide may either be directly spun or may initially be processed into a granulate which may then be further processed in known manner.

The following compounds are mentioned as examples of urethanes containing ether groups which are particularly suitable for use in the production of the antistatic polyamide compositions according to the invention, although the process is by no means confined to these particular compounds:

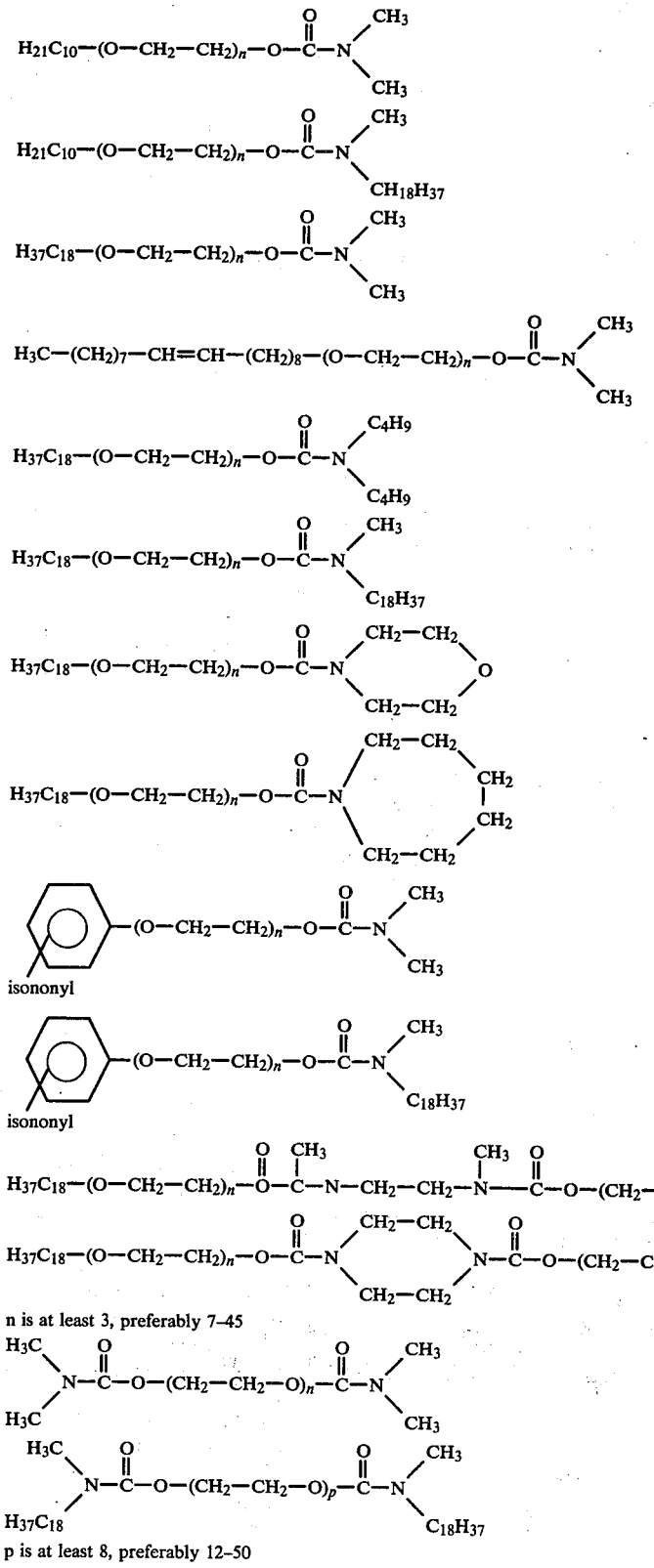

n is at least 3, preferably 7-45 p is at least 8, preferably 12-50

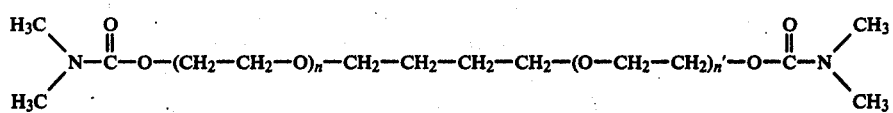
n + n' = 6-90
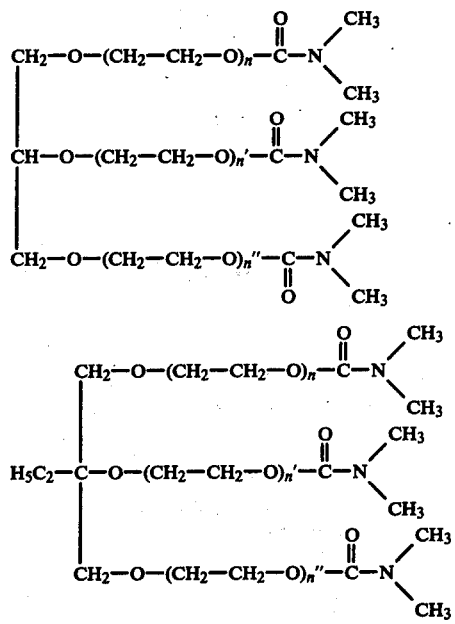
n, n', n'' = 3-45, n+n'+n'' = 9-135
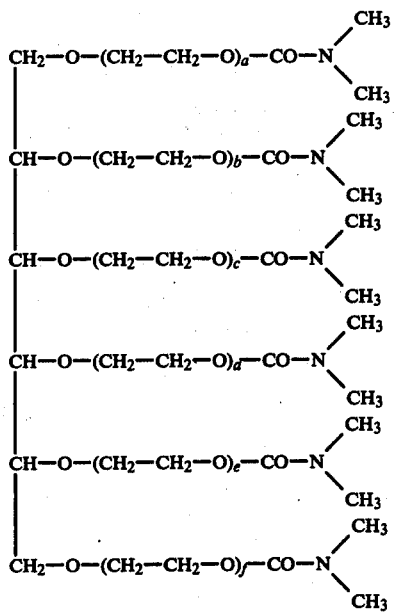
a, b, c, d, e, and f, independently of one another = 3-45,
a+b+c+d+e+f = 18-270
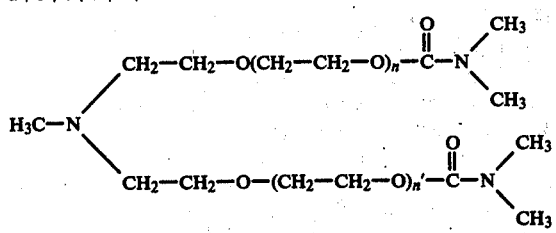
n and n' independently of one another = 7-45

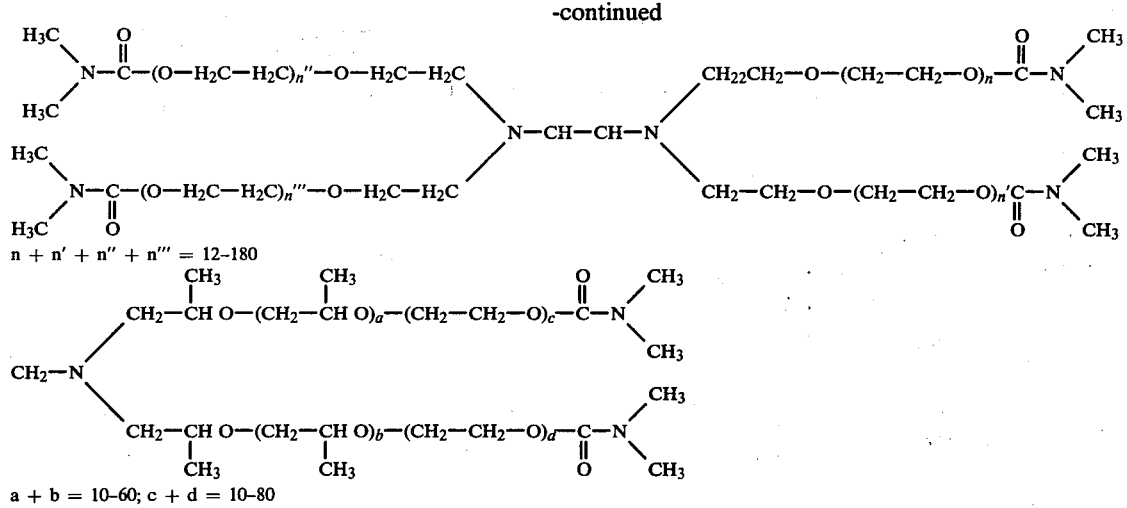

$n + n' + n'' + n''' = 12{-}180$ $a + b = 10{-}60; c + d = 10{-}80$

Polyalkylene ethers of this kind containing terminal urethane groups may be prepared by converting the corresponding polyalkylene ethers with one or more terminal hydroxyl groups into the chlorocarbonic acid esters with phosgene by conventional methods and subsequently reacting the chlorocarbonic acid esters with secondary amines, again by conventional methods, or by reacting the polyalkylene ethers with free terminal hydroxyl groups with the corresponding carbamic acid chlorides in the presence of basic compounds.

In cases where the reaction is carried out with a deficit of phosgene or carbamic acid chloride, compounds are obtained whose terminal hydroxyl groups have only been partly converted into the urethane groups. Compounds of this kind may also be used with advantage as antistatic agents in polyamides. However, it is better to select the quantities of the reacting components and also the reaction conditions in such a way that the terminal hydroxyl groups are converted substantially completely into urethane groups. The polyalkylene ethers with one or more hydroxyl groups used as starting compounds can be obtained, for example, by polymerising epoxides, for example ethylene oxide or propylene oxide or by subjecting epoxides of this kind to polyaddition with low molecular weight monohydric or polyhydric alcohols or monoamides or polyamides (cf. Houben Weyl, Methoden der organischen Chemie Vol. XIV/2, pages 426 to 462).

The described polyalkylene ethers with secondary urethane groups may also be used as antistatic agents in combination with other antistatic agents, for example with polyethoxylated stearyl alcohol, polyethoxylated nonyl phenol, polyethoxylated ethylene diamine or tertiary amides.

In addition to the antistatic agents, the antistatic polyamide compositions may also contain the usual additives, such as light stabilisers, heat stabilisers, fillers and/or pigments.

The polyalkylene glycol ethers containing terminal urethane groups are suitable for use as additives in any fusible, aliphatic polyamides, but especially in poly-ε-caproic amide.

The antistatic properties of the polyamide compositions according to the invention are reflected in a distinct reduction in electrical surface resistance. Electrical surface resistance is measured in accordance with DIN 54 345 on fibres, filaments or sheet-form materials.

The following Examples illustrate the production of the antistatic polyamide compositions and describe their properties, although neither the processes used nor the properties of the polyamide compositions thus obtained are intended to be limited in any way by the Examples. The relative viscosity ($\eta_{rel}$) quoted in the Examples was measured on a 1% solution in m-cresol. To this end, 1 g of polyamide was dissolved in 100 ml of m-cresol and the run-through time ($^{te}$) of the solution was measured in an Ubbelohde viscosimeter at 25° C. The relative viscosity $\eta_{rel}$ was then calculated from the equation: $\eta_{rel} = te/tem$ in which tem is the run-through time of the pure solvent.

The following Examples are to further illustrate the invention without limiting it.

EXAMPLE 1

(a) Preparation of the bis-dimethyl urethane of polyethylene glycol 1000

512.5 g (½ mol) of polyethylene glycol with a molecular weight of 1025 are dissolved in 4 liters of toluene at 30° C. 105 g of phosgene are introduced at 30° C. After stirring for 2 hours, nitrogen is blown through the solution for 3 hours at room temperature in order to remove the excess phosgene. 100 g of dimethylamine are then introduced into the solution at room temperature, followed by stirring for a few hours. The dimethylamine hydrochloride precipitated is filtered off under suction and the filtrate concentrated in vacuo. According to IR- and NMR-analysis, the residue which solidifies on cooling is the required bis-dimethyl urethane of the polyethylene glycol used.

(b) Production of the antistatic polyamide compositions 130 g of ε-caprolactam, 15 g of ε-aminocaproic acid and 3 g of the diurethane prepared in accordance with 1(a) are heated under nitrogen to 270° C. and condensed with intensive stirring for 3 hours at that temperature. The polyamide obtained is spun into filaments on which the following electrical surface resistances were measured in accordance with DIN 54 345:

After production: $5.10^9 \Omega \cdot cm^2$
After the first wash: $1.10^{11} \Omega \cdot cm^2$
After the fifth wash: $3.10^{11} \Omega \cdot cm^2$ Polycaprolactam without any antistatic additives has a surface resistance of approximately $5.10^{12} \Omega \cdot cm^2$ after only the first wash.

Polycaprolactam filaments which, instead of the diurethane, contain the same quantity of polyethylene glycol 1000 without any terminal urethane groups, have an electrical surface resistance of $7.10^{11}\Omega\cdot cm^2$ after the wash and an electrical surface resistance of $2.10^{12}\Omega\cdot cm^2$ after the fifth wash.

EXAMPLE 2

The procedure is as in Example 1(b) except that 7.5 g of diurethane are used instead of 3 g of diurethane. Filaments obtained from the resulting polyamide, which has a $\eta_{rel}$ of 2.85 (as measured on a 1% solution in cresol), have the following electrical surface resistance:

After production: $4.10^8\Omega\cdot cm^2$
After the first wash: $3.10^{10}\Omega\cdot cm^2$
After the fifth wash: $6.10^{10}\Omega\cdot cm^2$

EXAMPLE 3

130 g of ε-caprolactam 15 g of ε-aminocaproic acid and 3 g of a diurethane, obtained from polyethylene glycol of molecular weight 2050, phosgene and dimethyl amine in accordance with Example 1(a) are heated under nitrogen to 270° C. and condensed with intensive stirring for 4 hours at that temperature. Filaments obtained from this polyamide, which has a relative viscosity of 2.95 have the following electrical surface resistances:

After production: $1.10^9\Omega\cdot cm^2$
After the first wash: $5.10^{10}\Omega\cdot cm^2$
After the fifth wash: $9.10^{10}\Omega\cdot cm^2$ Polycaprolactam without any antistatic additives has an electrical surface resistance of $5.10^{12}\Omega\cdot cm^2$ after only one wash.

EXAMPLE 4

Example 3 is repeated with 7.5 g of the diurethane of the polyethylene glycol 2050. Filaments obtained from this polyamide composition were found by measurement to have the following electrical surface resistance:

After production: $6.10^8\Omega\cdot cm^2$
After the first wash: $3.10^{10}\Omega\cdot cm^2$
After the fifth wash: $6.10^{10}\Omega\cdot cm^2$ Polycaprolactam filaments which, instead of the diurethane, contain the same quantity of polyethylene glycol 2000 without any urethane groups, have an electrical surface resistance of $3.10^{10}\Omega\cdot cm^2$ after the first wash and an electrical surface resistance of $1.10^{11}\Omega\cdot cm^2$ after the fifth wash.

EXAMPLE 5

130 g of ε-caprolactam 15 g of ε-aminocaproic acid and 3 g of a dimethyl urethane, obtained from 10-fold ethoxylated isononyl phenol in accordance with Example 1(a), were heated under nitrogen to 270° C. and condensed with intensive stirring for 4 hours at that temperature. The polyamide composition obtained is processed into filaments on which the following electrical surface resistance were measured:

After production: $6.10^9\Omega\cdot cm^2$
After the first wash: $1.10^{11}\Omega\cdot cm^2$
After the fifth wash: $3.10^{11}\Omega\cdot cm^2$
After the tenth wash: $5.10^{11}\Omega\cdot cm^2$ Polycaprolactam without any antistatic additives has an electrical surface resistance of about $5.10^{12}\Omega\cdot cm^2$ after only one wash. Polycaprolactam filaments which, instead of the urethane contain the same quantity of 10-fold ethoxylated nonyl phenol without any urethane groups, have a surface resistance of $2.10^{11}\Omega\cdot cm^2$ after one wash and a surface resistance of as high as $2.10^{12}\Omega\cdot cm^2$ after only five washes.

EXAMPLE 6

Example 5 is repeated with 7.5 g of dimethyl urethane of the 10-fold ethoxylated isononyl phenol. Filaments were found by measurement to have the following electrical surface resistance:

After production: $9.10^8\Omega\cdot cm^2$
After the first wash: $3.10^{10}\Omega\cdot cm^2$
After the fifth wash: $7.10^{10}\Omega\cdot cm^2$
After the tenth wash: $7.10^{10}\Omega\cdot cm^2$

EXAMPLE 7

130 g of ε-caprolactam 15, g of ε-aminocaproic acid and 3 g of a dimethyl urethane, obtained from 18-fold ethoxylated isononyl phenol in accordance with Example 1(a) were condensed under the conditions described in Example 5. Filaments obtained from the resulting polyamide composition were found to have the following electrical surface resistance:

After production: $6.10^9\Omega\cdot cm^2$
After the first wash: $6.10^{10}\Omega\cdot cm^2$
After the fifth wash: $6.10^{10}\Omega\cdot cm^2$
After the tenth wash: $8.10^{10}\Omega\cdot cm^2$ Polycaprolactam filaments which, instead of the urethane, contain the same quantity of 18-fold ethoxylated isononyl phenol, have an electrical surface resistance of $6.10^{10}\Omega\cdot cm^2$ after the first wash and an electrical surface resistance of as high as $4.10^{11}\Omega\cdot cm^2$ after five washes.

EXAMPLE 8

Example 7 is repeated with 7.5 g of the dimethyl urethane of the 18-fold ethoxylated isononyl phenol. The following electrical surface resistance were measured on filaments obtained from the resulting polyamide composition:

After production: $4.10^9\Omega\cdot cm^2$
After the first wash: $9.10^9\Omega\cdot cm^2$
After the fifth wash: $1.10^{10}\Omega\cdot cm^2$
After the tenth wash: $2.10^{10}\Omega\cdot cm^2$

EXAMPLES 9 TO 11

The electrical surface resistance of filaments obtained from polyamide compositions prepared in accordance with Example 7, which contain similar urethanes of ethoxylated isononyl phenols, are shown in Table 1.

Table 1

| Example No. | Urethane Added | Quantity added % | after production | after the first wash | after the fifth wash | after the tenth wash |
|---|---|---|---|---|---|---|
| 9 |  | 2 | $3.10^9$ | $5.10^{10}$ | $6.10^{10}$ | $2.10^{11}$ |
| 10 | " | 5 | $1.10^9$ | $2.10^{10}$ | $2.10^{10}$ | $6.10^{10}$ |

Electrical surface resistance $\Omega\cdot cm^2$ iso $H_{19}C_9$—⟨benzene⟩—O—$(CH_2$—$CH_2$—$O)_{28}$—C(=O)—N(CH$_3$)(CH$_3$)

Table 1-continued

| Example No. | Urethane Added | Quantity added % | Electrical surface resistance $\Omega \cdot cm^2$ | | | |
|---|---|---|---|---|---|---|
| | | | after production | after the first wash | after the fifth wash | after the tenth wash |
| 11 | 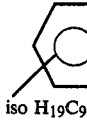 iso $H_{19}C_9$ | 2 | $5 \cdot 10^9$ | $8 \cdot 10^{10}$ | $1 \cdot 10^{10}$ | $2 \cdot 10^{11}$ |

EXAMPLE 12

130 g of ε-caprolactam, 15 g of ε-aminocaproic acid and 3 g of a dimethyl urethane, obtained from 20-fold ethoxylated stearyl alcohol, phosgene and dimethyl amine in accordance with Example 1(a), were heated under nitrogen to 270° C. and condensed with intensive stirring for 3.5 hours at that temperature. The polyamide composition obtained was processed into filaments on which the following electrical surface resistances were measured:
After production: $4 \cdot 10^9 \Omega \cdot cm^2$
After the first wash: $4 \cdot 10^{10} \Omega \cdot cm^2$
After the fifth wash: $4 \cdot 10^{10} \Omega \cdot cm^2$
After the tenth wash: $6 \cdot 10^{10} \Omega \cdot cm^2$

EXAMPLE 13

Example 12 is repeated with 7.5 g of the dimethyl urethane of 20-fold ethoxylated stearyl alcohol. The following electrical surface resistance were measured on filaments of this polyamide composition:

After production: $9 \cdot 10^8 \Omega \cdot cm^2$
After the first wash: $4 \cdot 10^9 \Omega \cdot cm^2$
After the fifth wash: $4 \cdot 10^9 \Omega \cdot cm^2$
After the tenth wash: $8 \cdot 10^9 \Omega \cdot cm^2$ Polycaprolactam filaments which, instead of the urethane, contain the same quantity of 20-fold ethoxylated stearyl alcohol without any urethane groups, have an electrical surface resistance of $2 \cdot 10^{10} \Omega \cdot cm^2$ after the first wash, a surface resistance of $3 \cdot 10^{10} \Omega \cdot cm^2$ after the fifth wash and a surface resistance of $8 \cdot 10^{10} \Omega \cdot cm^2$ after the tenth wash.

When the dimethyl urethane of 20-fold ethoxylated stearyl alcohol is applied in the form of a 5% preparation to finished polycaprolactam fibres without any antistatic additives, the electrical surface resistance rises to as high as $5 \cdot 10^{12} \Omega \cdot cm^2$ after only one wash.

EXAMPLES 14 TO 25

The electrical surface resistances of polyamide compositions which were prepared in accordance with Example 12 and which contain different polyalkylene ether urethanes, are shown in Table 2.

Table 2

| Ex. No. | Urethane added | Quantity added % | Electrical surface resistance $\Omega \cdot cm^{Ex.}$ | | | |
|---|---|---|---|---|---|---|
| | | | after production | after the first wash | after the fifth wash | after the tenth wash |
| 14 | $H_{37}C_{18}-O-(CH_2-CH_2-O)_7-\overset{O}{\underset{\|}{C}}-N\overset{CH_3}{\underset{CH_3}{\diagdown}}$ | 2 | $3 \cdot 10^9$ | $7 \cdot 10^{10}$ | $8 \cdot 10^{10}$ | $1 \cdot 10^{11}$ |
| 15 | " | 5 | $2 \cdot 10^9$ | $4 \cdot 10^{10}$ | $4 \cdot 10^{10}$ | $3 \cdot 10^{10}$ |
| 16 | " | 10 | $3 \cdot 10^9$ | $6 \cdot 10^9$ | $5 \cdot 10^9$ | $5 \cdot 10^9$ |
| 17 | $H_{37}C_{16}-O-(CH_2-CH_2-O)_{14}-\overset{O}{\underset{\|}{C}}-N\overset{CH_3}{\underset{CH_3}{\diagdown}}$ | 2 | $6 \cdot 10^9$ | $8 \cdot 10^{10}$ | $1 \cdot 10^{11}$ | $2 \cdot 10^{11}$ |
| 18 | $H_{37}C_{18}-O-(CH_2-CH_2-O)_{32}-\overset{O}{\underset{\|}{C}}-N\overset{CH_3}{\underset{CH_3}{\diagdown}}$ | 2 | $2 \cdot 10^9$ | $4 \cdot 10^{10}$ | $4 \cdot 10^{10}$ | $5 \cdot 10^{10}$ |
| 19 | " | 5 | $6 \cdot 10^8$ | $7 \cdot 10^9$ | $1 \cdot 10^{10}$ | $3 \cdot 10^{10}$ |
| 20 | $H_{37}C_{18}-O-(CH_2-CH_2-O)_{46}-\overset{O}{\underset{\|}{C}}-N\overset{CH_3}{\underset{CH_3}{\diagdown}}$ | 2 | $1 \cdot 10^{10}$ | $2 \cdot 10^{11}$ | $7 \cdot 10^{10}$ | $1 \cdot 10^{11}$ |
| 21 | $H_{21}C_{10}-O-(CH_2-CH_2-O)_{21}-\overset{O}{\underset{\|}{C}}-N\overset{CH_3}{\underset{C_{18}H_{37}}{\diagdown}}$ | 2 | $8 \cdot 10^9$ | $1 \cdot 10^{11}$ | $6 \cdot 10^{10}$ | $8 \cdot 10^{10}$ |
| 22 | $H_{25}C_{12}-O-(CH_2-CH_2-O)_{21}-\overset{O}{\underset{\|}{C}}-N\overset{CH_3}{\underset{C_{18}H_{37}}{\diagdown}}$ | 2 | $5 \cdot 10^9$ | $2 \cdot 10^{11}$ | $6 \cdot 10^{10}$ | $7 \cdot 10^{10}$ |
| 23 | $H_{37}C_{18}-O-(CH_2-CH_2-O)_{20}-\overset{O}{\underset{\|}{C}}-N\overset{CH_3}{\underset{C_{18}H_{37}}{\diagdown}}$ | 2 | $5 \cdot 10^9$ | $6 \cdot 10^{10}$ | $6 \cdot 10^{10}$ | $9 \cdot 10^{10}$ |
| 24 | " | 5 | $2 \cdot 10^9$ | $1 \cdot 10^{10}$ | $5 \cdot 10^{10}$ | $3 \cdot 10^{10}$ |

Table 2-continued

| Ex. No. | Urethane added | Quantity added % | Electrical surface resistance $\Omega \cdot cm^{Ex.}$ | | | |
|---|---|---|---|---|---|---|
| | | | after production | after the first wash | after the fifth wash | after the tenth wash |
| 25 | 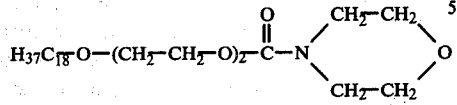 | 5 | $3.10^9$ | $2.10^{10}$ | $4.10^{10}$ | $5.10^{10}$ |

EXAMPLE 26

A mixture of 180 g of caprolactam, 10 g of ε-aminocaproic acid, 0.2 g of benzoic acid, 0.6 g of titanium dioxide and 10 g of stearyl 32-fold ethoxylated N,N-dimethyl urethane are heated under nitrogen for 2 hours to 260° C., followed by stirring for another 6 hours at that temperature. The resulting polycaprolactam, which has a relative viscosity of 2.55 in the form of a 1% solution in m-cresol, is processed into filaments which have the following surface resistances:
After production: $1.10^{10}\Omega \cdot cm^2$
After the fifth wash: $7.10^9\Omega \cdot cm^2$
After the tenth wash: $4.10^{10}\Omega \cdot cm^2$

EXAMPLE 27

A polycaprolactam granulate containing 0.33% by weight of titanium dioxide and having a relative viscosity (1% solution in m-cresol) of 2.66, is mixed with 5% by weight of stearyl 32-fold ethoxylated N,N-dibutyl urethane, and the resulting mixture is melted at 260° C., stirred homogeneously and processed into filaments which have a surface resitance of $2.10^{10}\Omega \cdot cm^2$, a surface resistance of $7.10^9\Omega \cdot cm^2$ after the fifth wash and a surface resistance of $3.10^{10}\Omega \cdot cm^2$ after the tenth wash.

EXAMPLE 28

130 g of ε-caprolactam, 15 g of ε-aminocaproic acid and 7.5 g of a dimethyl urethane, obtained in accordance with Example 1(a) from 19-fold ethoxylated oleyl alcohol, phosgene and dimethylamine, were heated under nitrogen to 270° C. and condensed with stirring for 3.5 hours at that temperature. The polyamide composition obtained was spun into filaments on which the following electrical surface resistances were measured:
After production: $1.10^9\Omega \cdot cm^2$
After the first wash: $2.10^{10}\Omega \cdot cm^2$
After the fifth wash: $5.10^{10}\Omega \cdot cm^2$
After the tenth wash: $4.10^{10}\Omega \cdot cm^2$ Examples 29 to 36 below describe the production of antistatic polyamide compositions according to the invention on a commercial scale.

EXAMPLES 29 TO 31

In a closed autoclave, caprolactam, water and the antistatic agent mentioned in Example 12, together with benzoic acid as a chain regulator and titanium dioxide concentrate, in the quantities specified in Table 3 are heated with stirring for 2 hours to 260° C. under the pressure developing. Over the next 30 minutes the temperature is increased to 265° C., and, at the same time, the autoclave is vented. Polycondensation is then completed by passing dry nitrogen over and stirring the reaction mixture for 2.5 hours. The melt is degassed for 30 minutes after which five 2 to 3 mm thick polyamide strands are spun into water over a period of 80 minutes, the strands thus spun subsequently being chopped into cylindrical granules 3 mm long.

The granulate is extracted with fully desalted water for 24 hours at 80° C. and subsequently dried for 24 hours at 95° C./0.1 Torr. After drying, the granulate has a moisture content of less than 0.07%.

Further details of the individual tests are set out in Table 3 below:

Table 3

| Example No. | Caprolactam kg | Water kg | Chain regulator mol | TiO₂ % | Antistatic additive % | Solution viscosity $\eta$rel | Antistatic content (a) % |
|---|---|---|---|---|---|---|---|
| 29 | 98.5 | 3.0 | 2.25 | 0.30 | 1.5 | 2.75 | 1.51 |
| 30 | 97.0 | 3.0 | 2.25 | 0.30 | 3.0 | 2.68 | 2.88 |
| 31 | 95.5 | 3.0 | 2.00 | 0.30 | 4.5 | 2.64 | 4.21 |

(a) = analytically determined

The granulates are melted at 283° C. in a 24 D extruder with a screw diameter of 30 mm, and are spun through a spinneret with 126 bores, each 0.30 mm in diameter. The spinning rate is 160 g per minute. The filaments are run off at a rate of 200 meters per minute and are wound into packages. After stretching in a ratio of 1:3.72, the surface resistance of the filaments can be determined in the same way as described above. The values quoted in Table 4 were measured:

Table 4

| Filaments of polyamide according to Example No. | Electrical surface resistance [$\Omega cm^2$] | | |
|---|---|---|---|
| | after the first wash | after the fifth wash | after the tenth wash |
| 29 | $2.10^{11}$ | $1.10^{11}$ | $2.10^{11}$ |
| 30 | $7.10^{10}$ | $6.10^{10}$ | $1.10^{11}$ |
| 31 | $4.10^{10}$ | $3.10^{10}$ | $6.10^{10}$ |

The filaments of Examples 29 to 31 were fixed in hot air and their electrical surface resistances were re-measured. The results are set out in Table 5.

Table 5

| Filaments of polyamide according to Example No. | Electrical surface resistance [$\Omega cm^2$] | | | |
|---|---|---|---|---|
| | after fixing | after the first wash | after the fifth wash | after the tenth wash |
| 29 | $2.10^{11}$ | $2.10^{11}$ | $2.10^{11}$ | $1.10^{11}$ |
| 30 | $8.10^{10}$ | $9.10^{10}$ | $8.10^{10}$ | $5.10^{10}$ |
| 31 | $4.10^{10}$ | $5.10^{10}$ | $5.10^{10}$ | $3.10^{10}$ |

The filaments of Examples 29 to 31 were fixed with saturated steam and were found to have the surface resistances quoted in Table 6.

Table 6

| Filaments of polyamide according to Example No. | Electrical surface resistance [$\Omega cm^2$] | | | |
|---|---|---|---|---|
| | after fixing | after the first wash | after the fifth wash | after the tenth wash |
| 29 | $2.10^{11}$ | $5.10^{11}$ | $4.10^{11}$ | $4.10^{11}$ |
| 30 | $6.10^{10}$ $2.10^{11}$ | $1.10^{11}$ | $1.10^{11}$ | |

Table 6-continued

| Filaments of polyamide according to Example No. | Electrical surface resistance [Ω·cm²] | | | |
|---|---|---|---|---|
| | after fixing | after the first wash | after the fifth wash | after the tenth wash |
| 31 | $4.10^{10}$ | $7.10^{10}$ | $5.10^{10}$ | $5.10^{10}$ |

After fixing with saturated steam, filaments which, instead of the diurethane, contain 4.5% of 20-fold ethoxylated stearyl alcohol as antistatic agent, have an electrical surface resistance of $3.10^{10}\Omega\cdot cm^2$ which, after only one wash, rises to $2.10^{11}\Omega\cdot cm^2$.

Following removal of the preparation from the filaments, the antistatic agent was isolated from the granules of Example 31 and from the filaments treated with saturated steam, and it was found by IR- and NMR-spectroscopy that the polyalkylene ether urethane originally used had remained unchanged.

The outstanding antistatic properties of fibres obtained from polyamide compositions according to Example 31 were also tested on tufted carpets and knitted fabrics.

A. Tufted Carpet Test

Fibres with an individual denier of 20 dtex and a staple length of 150 mm were processed into a yarn with a count of 3.5/1, from which a tufted velour carpet on a polyester backing was produced on a tufting machine with a division of 5/32, and subsequently piece-dyed. The backing was then consolidated first with a standard commercial-grade latex and then with a latex made conductive by the addition of carbon black. These carpets were then stored for 72 hours under conditions of 20° C./30% relative atmospheric humidity. The antistatic properties of the carpets were tested by measuring the charge picked up by a person walking over the carpets with rubber-soled and leather-soled shoes. The test person walking over the carpet was connected to a fully insulated metal plate by means of a conductive cable. The electrical charge developed by the test person walking over the carpet and transmitted to the metal plate was measured by means of a modulation measuring head, for example of Professor Schwenkhagen's design.

During measurement, the test carpet rested on a heavily insulated rubber mat (volume resistance according to DIN 54 345 $>10^{10}\Omega\cdot cm^2$).

A person walking over the carpet with a standard backing developed a maximum charge of 2000 volt·cm$^{-1}$ when wearing leather-soled shoes, and a maximum charge of 1700 volt·cm$^{-1}$ when wearing rubber-soled shoes. The maximum charge developed from the carpet with a conductive backing amounted to 1000 volt·cm$^{-1}$ in the case of leather-soled shoes and to 800 volt·cm$^{-1}$ in the case of rubber-soled shoes. Charges in excess of 10,000 volt·cm$^{-1}$ were measured on a carpet produced for comparison from unmodified polyamide fibres and backed in the usual way both when it was walked on with leather-soled shoes and when it was walked on with rubber-soled shoes.

When the standard backing was replaced by a conductive backing, the charge was reduced to 8000 volt·cm$^{-1}$. However, these values are still distinctly above the so-called perceptibility limit of 3000 volt·cm$^{-1}$ at which people generally sense shock-like discharges on coming into contact with articles of high capacity, such as door handles, typewriters, etc. These critical values are never reached in the case of carpets produced from fibres according to the invention.

B. Knitted Fabric Test

A warp knit fabric was produced from a dtex 44 f 10 filament yarn. A 15 cm wide strip of this fabric was fixed on one side to a metal clamp and, on its other side, was placed at an interval of 30 cm over a metal roller and loaded at an angle of 90° with a 1 kg weight. A rotating friction arm whose friction surface was covered with Dralon Fabric was moved over the taught, horizontal surface. After 10 strokes, the charge developed in the knitted fabric was measured as field strength by means of the modulation measuring head described above arranged at a distance of 3 cm. A charge of 600 volt·cm$^{-1}$ was measured on the knitted fabric produced from fibres according to the invention at 23° C./50% relative humidity. Half the charge produced had dissipated after less than 2 seconds. By contrast, the charge developed in a knitted fabric produced from unmodified polyamide filament yarn of the same denier amounted to 8000 volt·cm$^{-1}$ and had a half-life of 15 seconds. When a preparation-free woven polyester fabric was rubbed over the knitted fabric of filament yarn produced in accordance with the invention under conditions of 20° C./30% relative humidity, it did not adhere to the knitted fabric, whereas when the same fabric was rubbed over the comparison knitted fabric of unmodified polyamide filament yarn, the two pieces were still adhering to one another after as long as 60 seconds.

EXAMPLES 32 TO 35

Using the extruder described in the preceding Examples, chips with a relative solution viscosity of 2.9 are melted and spun under the same conditions. Some of the properties of the filament yarn obtained are shown in Table 7 for Example 32.

In Examples 33 to 35, the same antistatic agent as in the preceding Examples 29 to 31 in molten form is directly introduced into the chip inlet of the screw in the quantities specified in Table 7 by means of a piston metering pump (Lewa pump). The properties of these filament yarns are shown in Table 7 below.

Table 7

| Test No. | Antistatic additive | | Surface resistance after the first wash Ω. cm² | tensile strength p/dtex | elongation at break % |
|---|---|---|---|---|---|
| | quantity added % | analytically determined % | | | |
| 32 | 0 | 0 | $5.10^{12}$ | 4.6 | 36 |
| 33 | 1.5 | 1.45 | $1.10^{11}$ | 4.7 | 38 |
| 34 | 3.0 | 2.87 | $7.10^{10}$ | 4.5 | 40 |
| 35 | 4.5 | 4.23 | $4.10^{10}$ | 4.5 | 36 |

EXAMPLE 36

3% of the antistatic additive used in Example 12 are mixed into the monomer-free melt from a VK tube (cf. Hermann Klare, Synthetische Fasern aus Polyamiden, Akademie-Verlag, Berlin 1973) both by means of a piston metering pump (cf. Examples 33–35) and by means of a dynamic mixer of the type described in DT-AS No. 1,557,064 (laid open on the 16.11.1972).

The melt is further processed under the same conditions as in Examples 29 to 31.

The measurement results are set out in Table 8.

Table 8

| Test No. | Antistatic additive quantity added % | Antistatic additive analytically determined % | Surface resistance after the first wash Ω·cm² | tensile strength p/dtex | elongation at break % |
|---|---|---|---|---|---|
| 30 | 3.0 | 2.95 | 6.10¹⁰ | 4.6 | 38 |

EXAMPLE 37

(a) Preparation of a diurethane from 20-fold ethoxylated stearyl alcohol and N,N'-dimethyl ethylene diamine 585 g of 20-fold ethoxylated stearyl alcohol were dissolved in 1.5 liters of toluene. 60 g of phosgene were introduced at 50° C., followed by rinsing with nitrogen. A slight haze was removed by filtration under suction. The solution was concentrated, a temperature of 130° C. and a vacuum of 15 Torr ultimately being applied. The chlorocarbonic acid ester of the 20-fold ethoxylated stearyl alcohol was left as residue in a substantially quantitative yield. 246 g of this chlorocarbonic acid ester were dissolved in 400 ml of benzene. The resulting solution was then added dropwise to a solution, cooled to 5°–10° C., of 9 g of N,N'-dimethyl ethylene diamine and 35 g of triethylamine in 200 ml of benzene. The mixture was then stirred for 2 hours at 50° C. The triethylamine hydrochloride was filtered off under suction. The filtrate was concentrated. IR-examination and analysis showed that the desired compound had been obtained.

(b) Production of the antistatic polyamide composition 130 g of ε-caprolactam, 15 g, of ε-aminocaproic acid and 7.5 g of the diurethane prepared in accordance with (a) were heated under nitrogen to 270° C. and condensed with intensive stirring for 4 hours at that temperature. The polyamide composition obtained ($\eta_{rel}$=2.66) was processed into filaments on which the following electrical surface resistances were determined:

After production: 2.10⁹Ω·cm²
After the first wash: 3.10¹⁰Ω·cm²
After the fifth wash: 6.10¹⁰Ω·cm²
After the tenth wash: 5.10¹⁰Ω·cm²

EXAMPLE 38

(a) Preparation of a diurethane from 20-fold ethoxylated stearyl alcohol and piperazine 20-fold ethoxylated stearyl alcohol was converted into the chlorocarbonic acid ester in the same way as described in Example 37a). 123 g of this chlorocarbonic acid ester were dissolved in 600 ml of water. The resulting solution and a 30% NaOH-solution were simultaneously added dropwise to a solution of 9.7 g of piperazine hexahydrate in 300 ml of water, the dropwise addition being made in such a way that the pH-value of the solution was always between 10 and 10.5. On completion of the addition, the reaction mixture was stirred for 1 hour, after which a pH-value of 7 was adjusted with concentrated hydrochloric acid. The water was distilled off, the residue was taken up in 600 ml of dioxan, the sodium chloride was filtered off and the filtrate was concentrated. 120 g of residue were obtained. According to analysis and IR-examination, the residue was the desired diurethane.

(b) Production of the antistatic polyamide composition 130 g of ε-caprolactam, 15 g of ε-aminocaproic acid and 7.5 g of the diurethane produced in accordance with 38(a) were heated under nitrogen to 270° C. and condensed with intensive stirring for 4 hours at that temperature. The polyamide composition obtained ($\eta_{rel}$=2.41) was processed into filaments on which the following electrical surface resistances were measured:

After production: 3.10⁹Ω·cm²
After the first wash: 3.10¹⁰Ω·cm²
After the fifth wash: 7.10¹⁰Ω·cm²
After the tenth wash: 6.10¹⁰Ω·cm²

EXAMPLE 39

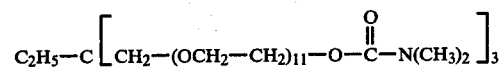

14.2 kg of 33-fold ethoxylated trimethylol propane of molecular weight 1586 are dissolved with stirring in 30 liters of toluene. 3.12 kg of phosgene are introduced at 0° to 10° C. and the temperature allowed to rise slowly to 20° C., followed by stirring for another 3 hours. The excess phosgene and the hydrogen chloride formed are then blown off with nitrogen at a temperature of approximately 80° C. 2.3 kg of dimethylamine are then introduced at 20° to 30° C. and 2 kg of a 50% aqueous sodium hydroxide solution added dropwise, followed by stirring for 3 hours. For working up, the water is separated off azeotropically through a water separator. After filtration to isolate the sodium chloride precipitated, the toluene is removed by distillation, ultimately in vacuo.

| Analysis | C | H | N |
|---|---|---|---|
| calculated | 54.1 | 8.9 | 2.3 |
| found | 54.3 | 9.3 | 2.2 |

5% of the urethane formed are worked into polycapronamide as in Example 26 and the melt is spun into filaments. The filaments thus obtained have the following surface resistances:

After production: 2.10⁹Ω·cm²
After the first wash: 3.10¹⁰Ω·cm²
After the fifth wash: 5.10¹⁰Ω·cm²
After the tenth wash: 5.10¹⁰Ω·cm²

Polycapronamide fibres containing 5% of the starting product without any urethane groups have a surface resistance of 2.10¹¹Ω·cm² after ten washes.

EXAMPLE 40

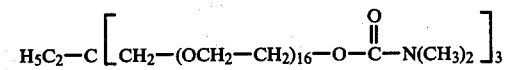

The triurethane is prepared as in Example 1 from 48-fold ethoxylated trimethylol propane, phosgene and dimethylamine. The IR-spectrum of the product does not show an OH-band.

Polycapronamide filaments containing 5% of this substance have the following surface resistances:

After the first wash: 4.10¹⁰Ω·cm²
After the third wash: 8.10¹⁰Ω·cm²
After the fifth wash: 8.10¹⁰Ω·cm²
After the tenth wash: 5.10¹⁰Ω·cm²

Polycapronamide fibres containing 5% of the starting product without any urethane groups have a surface resistance of 2·10¹¹Ω·cm² after ten washes.

EXAMPLE 41

$$H_5C_2-C\left[CH_2-(OCH_2-CH_2)_{5.5}-O-\overset{O}{\underset{\|}{C}}-N-(CH_3)_2\right]_3$$

The triurethane is prepared as in Example 1 from 16.5-fold ethoxylated trimethylol propane, phosgene and dimethylamine. The IR-spectrum of the product does not show an OH-band Polycapronamide filaments containing 5% of this substance show the following surface resistances.
  After the first wash: $6.10^{10}\Omega\cdot cm^2$
  After the third wash: $7.10^{10}\Omega\cdot cm^2$
  After the fifth wash: $9.10^{10}\Omega\cdot cm^2$
  After the tenth wash: $7.10^{10}\Omega\cdot cm^2$

EXAMPLE 42

$$H_5C_2-C\left[CH_2-(O-CH_2-\underset{CH_3}{\overset{|}{CH}})_7-(OCH_2-CH_2)_{10}-O-\overset{O}{\underset{\|}{C}}-N(CH_3)_2\right]_3$$

2500 g (1.0 mol) of trimethylol propane, to which a total of 21 equivalents of propylene oxide to begin with and then 30 equivalents of ethylene oxide were added, are dissolved in 5 liters of benzene. 372 g (3.75 mol) of phosgene are introduced at 20° to 30° C., followed by stirring for 4 hours at 20° C. The rest of the phosgene and the hydrogen chloride formed are removed by a vigorous stream of nitrogen. 205 g (4.5 mols) of dimethylamine are then introduced and the hydrochloride is precipitated. 240 g of a 50% sodium hydroxide solution (corresponding to 3.0 mols of NaOH) are then added dropwise, followed by stirring for 5 hours at 50° C. The salt is filtered off and the aqueous phase is separated. The benzene is then distilled off under normal pressure, ultimately in vacuo.

Polycapronamide filaments containg 5% of this substance have the following surface resistances:
  After the first wash: $5.10^{10}\Omega\cdot cm^2$
  After the third wash: $6.10^{10}\Omega\cdot cm^2$
  After the fifth wash: $6.10^{10}\Omega\cdot cm^2$
  After the tenth wash: $5.10^{10}\Omega\cdot cm^2$

EXAMPLE 43

$$\left[(H_3C)_2-N-\overset{O}{\underset{\|}{C}}(OCH_2-CH_2)_{\overline{15}}(O\underset{CH_3}{\overset{|}{CH}}-CH_2)_{17}\right]_2N-CH_2$$
$$\left[(H_3C)_2-N-\overset{O}{\underset{\|}{C}}(OCH_2-CH_2)_{\overline{15}}(O\underset{CH_3}{\overset{|}{CH}}-CH_2)_{17}\right]_2N-CH_2$$

1700 g (0.25 mol) of an ethylene diamine, to which a total of 68 equivalents of propylene oxide to begin with and then 60 equivalents of ethylene oxide were added, are dissolved in approximately 1.5 liters of benzene. 200 g (2.0 mols) of phosgene are introduced at 20° C. and, after stirring for 3 hours at 30° C., the excess phosgene and some of the hydrogen chloride formed are removed with a vigorous stream of nitrogen. 250 g of dimethylamine are then introduced, after which the solution should show an alkaline reaction. After stirring for 5 hours at 50° C., the solution is filtered off under suction from the hydroxhloride precipitated, diluted with another 3 liters of benzene and washed once with approximately 300 ml of a 5% sodium carbonate solution. The solution is then washed until neutral with saturated sodium chloride solution, after which the benzene is distilled off. The residue is taken up in ethanol, filtered off from the sodium chloride and reconcentrated.

Polycapronamide filaments containing 5% of this tetraurethane have the following surface resistances:
  After production: $5.10^9\Omega\cdot cm^2$
  After the first wash: $2.10^{11}\Omega\cdot cm^2$
  After the fifth wash: $9.10^{10}\Omega\cdot cm^2$
  After the tenth wash: $8.10^{10}\Omega\cdot cm^2$

EXAMPLE 44

(a) Preparation of a dimethyl urethane corresponding to the formula $$\begin{array}{l}
H_3C\diagdown\overset{O}{\underset{\|}{N-C}}-(O-CH_2-CH_2)_b-\overset{H}{\underset{|}{C}}-CH_2-O-(CH_2-CH_2-O)_a-\overset{O}{\underset{\|}{C}}-N\diagup\overset{CH_3}{\diagdown CH_3}\\
H_3C\diagup\\
H_3C\diagdown\overset{O}{\underset{\|}{N-C}}-(O-CH_2-CH_2)_c-\overset{O}{\underset{\|}{C}}-CH\\
H_3C\diagup\qquad\qquad\qquad\qquad\qquad\quad |\\
\qquad\qquad\qquad\qquad\qquad\qquad CH-O-(CH_2-CH_2-O)_d-\overset{O}{\underset{\|}{C}}-N\diagup\overset{CH_3}{\diagdown CH_3}\\
\qquad\qquad\qquad\qquad\qquad\qquad |\\
\qquad\qquad\qquad\qquad\qquad\qquad CH-O-(CH_2-CH_2-O)_e-\overset{O}{\underset{\|}{C}}-N\diagup\overset{CH_3}{\diagdown CH_3}\\
\qquad\qquad\qquad\qquad\qquad\qquad |\\
\qquad\qquad\qquad\qquad\qquad\qquad CH_2-O-(CH_2-CH_2-O)_f-\overset{O}{\underset{\|}{C}}-N\diagup\overset{CH_3}{\diagdown CH_3}
\end{array}$$

$a + b + c + d + e + f = 84$ 18.2 g of mannitol were treated with ethylene oxide at 170° C. in the presence of 0.1 g of solid NaOH until about 370 g of ethylene oxide have been taken up, so that an average of about 14 —O—CH$_2$—CH$_2$ groups were present per hydroxyl group of the mannitol. The residue was taken up in 2 liters of toluene, and 75 g of phosgene were then introduced into the resulting solution at 50° C. The excess phosgene and the hydrochloric acid formed were then blown out with nitrogen. 90 g of dimethylamine were then introduced into the solution at 30° C. The solution was then filtered off from the dimethylamine hydrochloride precipitated and the toluene was subsequently distilled off, a water jet vacuum being applied towards the end of distillation. According to IR-measurements, the residue left is free from OH-groups.

| Analysis | N |
|---|---|
| calculated | 1.87% |
| found | 1.90% |

(b) 130 g of ε-caprolactam, 15 g of ε-aminocaproic acid and 7.5 g of the dimethyl urethane prepared in accordance with (a) were condensed under the conditions of Example 5. Filaments obtained from the resulting polyamide composition were found to have the following electrical surface resistances:

After production: 2.10$^9$Ω·cm$^2$
After the first wash: 4.10$^{10}$Ω·cm$^2$
After the second wash: 6.10$^{10}$Ω·cm$^2$
After the third wash: 7.10$^{10}$Ω·cm$^2$ Polycaprolactam filaments which, instead of the urethane, contain the same quantity of the thoxylated mannitol produced in accordance with (a) which had not yet been further reacted to the dimethyl urethane, have an electrical surface resistance of 7.10$^{10}$Ω·cm$^2$ after the first wash, and an electrical surface resistance of as high as 2.10$^{11}$Ω·cm$^2$ after only the third wash.

What we claim is:

1. An antistatic polyamide composition consisting essentially of a polycarbonamide and, as an antistatic agent, from 0.5 to 20% by weight, based on said polycarbonamide, of a polyalkylene glycol ether with secondary terminal urethane groups corresponding to the general formula:

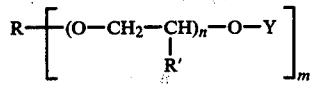

in which
m is a number of from 1 to 6;
n is a number of from 3 to 60;
R is an m-functional radical selected from the group consisting of alkyl, cycloalkyl, alkenyl, aralkyl, aryl, alkaryl, or any of alkyl, cycloalkyl, and alkenyl containing oxygen or nitrogen as a hetero atom;
R additionally is Y when m=1;
R' is hydrogen, C$_1$-C$_5$-alkyl, cycloalkyl, aryl, alkaryl, or aralkyl;
Y is hydrogen or

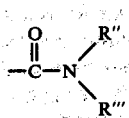

provided that at least 70% of the Y radicals are

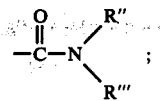

R'' and R''', independently of each other, are C$_1$-C$_{30}$-alkyl, cycloalkyl, aryl, aralkyl, alkaryl;
R'' and R''' additionally are C$_1$-C$_{30}$-alkyl interrupted by nitrogen or oxygen as a hetero atom, or are joined together to form a heterocyclic ring containing nitrogen or oxygen as a hetero atom.

2. The composition of claim 1 wherein

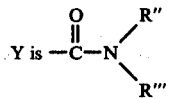

R is C$_1$-C$_{30}$-alkyl, C$_2$-C$_{30}$-alkenyl, aryl or alkaryl;
R' is hydrogen or C$_1$-C$_5$-alkyl;
R'' and R''', independently of each other are C$_1$-C$_{20}$-alkyl, or are joined together to form a heterocyclic ring containing (1) one or more nitrogen atoms or (2) at least one nitrogen atom and at least one oxygen atom as hetero atoms.

3. The composition of claim 1, which contains as an antistatic agent from 0.5 to 20% by weight of a polyalkylene glycol ether with terminal urethane groups corresponding to the formula:

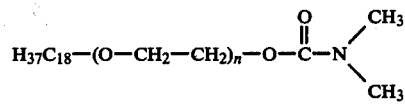

in which n is a number of 7–45.

4. The composition of claim 1, which contains as an antistatic agent from 0.5 to 20% by weight of a polyalkylene glycol ether having the formula

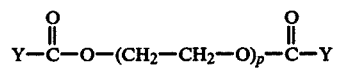

in
which p is a number from 8 to 50;
Y is

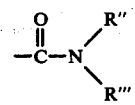

or hydrogen, at least 70% of the radicals Y being

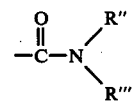

and R'' and R''', independently of one another, are C$_1$-C$_{30}$-alkyl, cycloalkyl, aryl, aralkyl or alkaryl or, when taken together, form a heterocyclic ring.

5. The composition of claim 1, which contains as an antistatic agent from 0.5 to 20% by weight of a polyalkylene glycol ether having the formula:

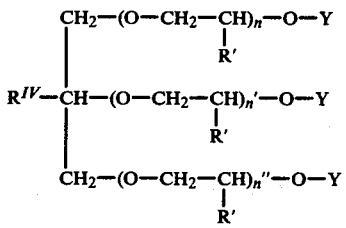

in which
n, n' and n", independently of one another, are numbers from 3 to 50, the sum of which totals at least 10;
R' is hydrogen $C_1$-$C_5$-alkyl;
$R^{IV}$ is hydrogen $C_1$-$C_{18}$-alkyl or aryl;
Y is

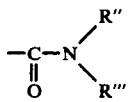

or hydrogen, at least 70% of the radicals Y being

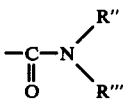

and R" and R''', independently of one another, are $C_1$-$C_{30}$-alkyl, cycloalkyl, aryl, aralkyl, or alkaryl, or, when taken together, form a heterocyclic ring.

6. The composition of claim 1, which contains as an antistatic agent from 0.5 to 20% by weight of a polyalkylene glycol ether having the formula:

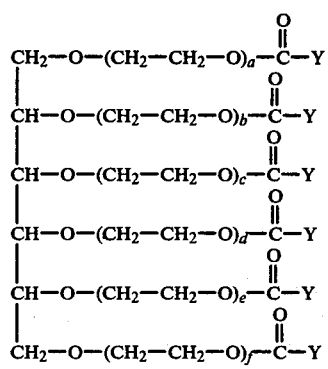

in which
a, b, c, d, e and f, independently of one another are numbers from 3 to 45, the sum of which totals at least 18;
Y is

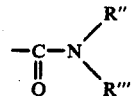

or hydrogen, at least 70% of the radicals being

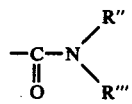

and R" and R''', independently of one another, are $C_1$-$C_{30}$-alkyl, cycloalkyl, aryl, aralkyl, or alkaryl, or, when taken together form a heterocyclic ring.

7. The composition of claim 1, which contains as an antistatic agent from 0.5 to 20% by weight of a polyalkylene glycol ether having the formula:

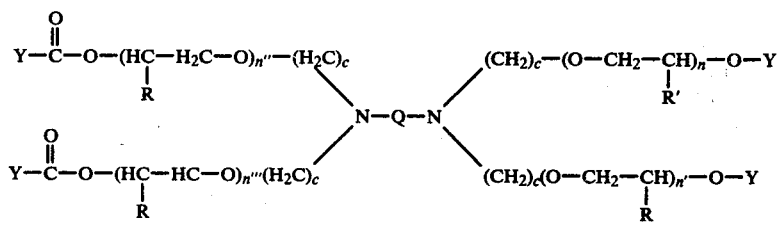

in which
c is a number from 2 to 6;
n, n", and n''', independently of one another, are numbers from 3 to 50, the sum of which totals at least 15;
R' is hydrogen or $C_1$-$C_5$-alkyl;
Q is $C_2$-$C_{10}$-alkylene, $C_2$-$C_{10}$-alkylene whose carbon chain is interrupted by nitrogen or oxygen as hetero atoms, or arylene;
Y is

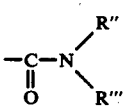

or hydrogen, at least 70% of the radicals Y being

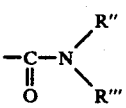

and R" and R''', independently of one another, are $C_1$-$C_{30}$-alkyl, cycloalkyl, aryl, aralkyl, or alkaryl, or, when taken together form a heterocyclic ring.

8. An antistatic polyamide composition consisting essentially of a polycarbonamide and, as an antistatic agent from 0.5 to 20% by weight of a polyalkylene glycol ether with secondary urethane groups having the formula:

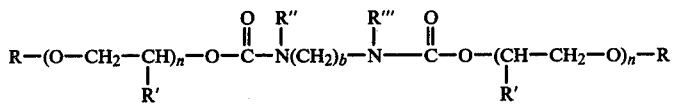
in which
n and n' are numbers from 3 to 60;
b is a number from 2 to 10;
R is $C_1$-$C_{30}$-alkyl, $C_2$-$C_{30}$-alkenyl, aryl, or alkaryl;
R' is hydrogen or $C_1$-$C_5$-alkyl;
R'' and R''', independently of each other, are $C_1$-$C_{20}$-alkyl, or, when taken together, are alkylene.
* * * * *

UNITED STATES PATENT AND TRADEMARK OFFICE
CERTIFICATE OF CORRECTION

PATENT NO. : 4,163,088
DATED : July 31, 1979
INVENTOR(S) : KÜNZEL et al.

It is certified that error appears in the above-identified patent and that said Letters Patent are hereby corrected as shown below:

Column 4, line 12, "urethane" should read -- urethanes --.

Column 18, Table 6, Example 30, in first wash column, delete "$1.10^{11}$" and insert -- $2.10^{11}$ -- and in tenth wash column, insert -- $1.10^{11}$ --.

Signed and Sealed this

*Twenty-fifth* Day of *December 1979*

[SEAL]

Attest:

Attesting Officer

SIDNEY A. DIAMOND

*Commissioner of Patents and Trademarks*